United States Patent [19]

Whelan

[11] 4,081,519
[45] Mar. 28, 1978

[54] PROCESS FOR OXIDATION OF CARBON MONOXIDE WITH INORGANIC OXIDIZING AGENTS

[75] Inventor: James M. Whelan, La Canada, Calif.

[73] Assignee: University of Southern California, Los Angeles, Calif.

[21] Appl. No.: 712,001

[22] Filed: Aug. 5, 1976

Related U.S. Application Data

[62] Division of Ser. No. 556,670, Mar. 10, 1975, Pat. No. 3,976,599, which is a division of Ser. No. 194,769, Oct. 8, 1971, Pat. No. 3,885,020.

[51] Int. Cl.$^2$ ............................................. C01B 31/20
[52] U.S. Cl. .................................. 423/437; 423/570; 423/655
[58] Field of Search ............... 423/210, 351, 247, 437, 423/655, 570, 239, 244; 252/462

[56] References Cited

U.S. PATENT DOCUMENTS

| 3,885,020 | 5/1975 | Whelan | 423/239 |
| 3,926,854 | 12/1975 | Whelan et al. | 423/213.5 |

*Primary Examiner*—Earl C. Thomas
*Attorney, Agent, or Firm*—Harris, Kern, Wallen & Tinsley

[57] ABSTRACT

A process for the oxidation of carbon monoxide to carbon dioxide with an inorganic oxidizing agent selected from the group consisting of water, nitric oxide and sulfur dioxide, which comprises combining the carbon monoxide with a predetermined amount of said oxidizing agent to give at least a stoichiometric amount of the oxidizing agent for the oxidation of the carbon monoxide to carbon dioxide, and passing the mixture over a novel ceramic catalyst at an elevated temperature.

4 Claims, No Drawings

PROCESS FOR OXIDATION OF CARBON MONOXIDE WITH INORGANIC OXIDIZING AGENTS

BACKGROUND OF THE INVENTION

This application is a division of application Ser. No. 556,670, filed Mar. 10, 1975, now U.S. Pat. No. 3,976,599, which is a division of Ser. No. 194,769, filed Oct. 8, 1971, now U.S. Pat. No. 3,885,020.

A class of ceramic mixed oxide, nonstoichiometric electrically neutral, rare-earth-type catalyst containing rare-earth-type elements, elements of the first transition metal series and Zirconium, Tin or Thorium and optimally the alkaline earth metals. The catalyst has the following formula:

$$W_k X_{m'} J_{(1-k-n)} Z_O (3 \pm m') \qquad (I)$$

wherein:
W is Zirconium, Tin or Thorium or mixture thereof;
X is an alkaline earth metal or mixture thereof;
J is scandium, yttrium, rare-earth element or mixture thereof;
Z is a metal of the first transition series or a mixture thereof, at least 0.01% of said metal having an oxidation state other than +3;
$k$ is a number having a value of between 0 and about 0.1;
$m'$ is a number having a value of from 0 to about 0.26, provided $m$ has a value other than 0 when $n$ has a value of 0; and
$n$ is a number having a value from 0 to about 0.51, provided when $n$ has a value of 0, $k$ has a value of between 0 and about 0.05. These mixed oxide catalysts can be used to catalytically oxidize organic compounds to various states of oxidation, ammonia, carbon monoxide, hydrogen, sulfur dioxide, and hydrogen sulfide, with oxygen, or carbon monoxide with water, sulfur dioxide or nitric oxide. The catalyst can also be employed in the catalytic removal of carbon monoxide, hydrocarbons, nitric oxides and sulfur dioxide from the exhaust gases of generating or heating plants and automobiles burning fossil fuels. In addition these catalysts can be employed to produce hydrogen cyanide from methane, ammonia and oxygen.

This invention is directed to a class of oxidation catalysts, to catalytic oxidation processes utilizing oxidation catalysts, and to methods of catalytically treating exhaust gases with oxidation catalysts to produce exhaust gases substantially free of harmful pollutants.

More particularly, the present invention is directed to a class of ceramic, mixed oxide, nonstoichiometric electrically neutral, oxidation catalysts of the following formula:

$$W_k X_{m'} J_{(1-k-n)} Z_O (3 \pm m') \qquad (I)$$

wherein:
W is Zirconium, Tin or Thorium or mixture thereof;
X is an alkaline earth metal or mixture thereof;
J is scandium, yttrium, rare-earth element or mixture thereof;
Z is a metal of the first transition series or a mixture thereof, at least 0.01% of said metal having an oxidation state other than ±3;
$k$ is a number having a value of between 0 and about 0.1;
$m'$ is a number having a value of from 0 to about 0.26, provided $m$ has a value other than 0 when $n$ has a value of 0; and
$n$ is a number having a value from 0 to about 0.51, provided when $n$ has a value of 0, $k$ has a value of between 0 and about 0.05.

In addition, the present invention is directed to processes for the catalytic oxidation of organic compounds to various states of oxidation, ammonia, carbon monoxide, hydrogen, hydrocarbons, sulfur dioxide and hydrogen sulfide with oxygen; of carbon monoxide with water vapor, sulfur dioxide or nitric oxide; and of a gaseous mixture of uncombusted or partially combusted fossil fuel, carbon monoxide, carbon dioxide and atmospheric gases with oxygen without the concomitant production and emission of nitric oxide in the exhaust gas, employing the catalyst described herein. Furthermore, the present invention is directed to methods of treating exhaust gases from chemical plants, electrical utility generating plants, heating plants, steel mills, smelting plants, trucks and automobiles to remove gaseous pollutants, such as carbon monoxide, hydrocarbons, partially oxidized hydrocarbons, the oxides of nitrogen, and sulfur dioxide, and hydrogen sulfide therefrom.

Since the advent of modern technology, air pollution has become a serious and tragic problem for man. The present industrial plants and automobiles which burn the fossil fuels emit a staggering amount of gaseous pollutants, principally unburned or partially burned fossil fuels, carbon monoxide, the oxides of nitrogen, sulfur dioxide and ozone. These pollutants are chemically reactive and have been found to be harmful to both plant life and animal life. Under certain weather conditions, the accumulative emissions of these pollutants can have tragic effects. For example, in late 1930 about 60 people died and another 6,000 became seriously ill from breathing abnormally high levels of gaseous pollutants in the Muse Ruhr Valley of Belgium. A more recent calamity took place in the mill town of Donora, Pennsylvania, in 1948. The death smogs or fogs that hovered over London, England, in 1952 and 1962 are well documented. As stated above, gaseous pollutants not only affect animal life but they also affect plant life. Smog has been found to have a serious effect on the evergreen trees growing on the mountain sides surrounding the Los Angeles basin. Furthermore, the University of California Air Pollution Research Center has found that smog has a detrimental effect on the growth and the fruit yield of citrus trees.

Smog is a by-product of a complex series of photosynthetic reactions that occur in the atmosphere when certain molecular species are found therein. More particularly it has been found that the production of photochemical smog requires nitrogen oxides such as nitric oxide and nitrogen dioxide, hydrocarbons, and ultraviolet light. One of the possible routes for the production of smog is theorized as follows: During the combustion of a fossil fuel the oxides of nitrogen are formed. These nitrogen oxides and some unburned fuel together with carbon monoxide are emitted in the exhaust gases. In the presence of hydrocarbons and sunlight the nitric oxide is photochemically oxidized to nitrogen dioxide. The nitrogen dioxide molecule is then photochemically split into nitric oxide and atomic oxygen. A portion of the atomic oxygen in turn interacts with molecular oxygen to form ozone or with hydrocarbons to form complex and reactive oxidation products. It then appears that a portion of the ozone reacts with the nitric oxide to provide a fresh supply of nitrogen dioxide. Another portion of the atomic oxygen and a portion of the reactive hydrocarbon oxidation products in the air form free radicals which in turn react very readily with oxygen, nitric oxide, nitrogen dioxide, and with other hydrocarbons to form more complex materials such as peroxyacyl nitrates. The peroxyacyl nitrates are suspected of being the principal cause of the eye-searing effect of smog; it has been documented that these compounds can cause substantial damage to crops when present in exceedingly small amounts, such as parts per hundred million.

From the time the primary gaseous pollutants known to cause photochemical smog were identified, it has been recognized that the elimination of these gaseous pollutants from the exhaust of industrial plants and vehicles would substantially eliminate photochemical smog. The chemical industry has been working diligently in this field over the last decade in an effort to accomplish this result. Some of the effort has resulted in the introduction of devices that give limited results, such as the smog-emission devices introduced on automobiles in the late 1960's. Other efforts have been directed toward catalysts and catalytic systems which can reduce the amount of hydrocarbons, carbon monoxide and nitric oxide emitted from the exhaust gas of motor vehicles and industrial plants burning fossil fuels. This effort has only been partially successful for a variety of reasons. For example, many of the catalysts developed were prepared from precious metals such as platinum and palladium; the resulting catalysts are relatively expensive. Many catalysts are readily deactivated by sulfur, oxygenated sulfur compounds or metals, such as lead. Other catalysts are environmentally and/or chemically sensitive and are rapidly inactivated when operated at high temperatures or in the presence of certain materials. Many of the present catalysts are only effective at low space velocities and can only be utilized in a catalytic system having a large catalytic bed and catalytic chamber to provide sufficient contact time between the exhaust gases and the catalyst. The catalytic systems that have been developed are generally quite complex and require more than one catalyst with each catalyst operating within a particular temperature range. To our knowledge no catalytic system has been developed for the removal of the major gas pollutants from fossil fuel exhaust fumes utilizing one catalyst which can effectively operate over a broad temperature of the exhaust gases.

An object of the present invention is to provide an oxidation catalyst which exhibits excellent efficiencies over a broad temperature range and at high space velocities. More particularly, it is an object to provide an oxidation catalyst that exhibits excellent chemical and thermal stability.

Another object of the present invention is to provide an oxidation catalyst which is effective in selectively oxidizing a broad range of molecular species, such as ammonia, carbon monoxide, hydrocarbons, and the like. More particularly, it is an object to provide an oxidation catalyst that can be used in the treatment of exhaust gases from industrial plants and motorized vehicles utilizing fossil fuels for the removal of substantially all carbon monoxide, combusted and partially combusted hydrocarbons, oxygenated hydrocarbons and oxides of nitrogen therefrom.

Ceramic, stoichiometric compounds of the following empirical formula are known and have been used in high temperature electrodes:

$$X'_n J'_{(1-n)} Z' O_3,$$

wherein
X' is Strontium;
J' is Yttrium or Lanthanum,
Z' is a metal of the first transition series, and
n is 0 or 0.22.

W. F. Libby has suggested that one of these catalysts ($LaCoO_3$) might be a promising catalyst for Auto Exhaust. However, he furnished no data to support this suggestion [see Science, Vol. 171, pages 499–500 (1971)].

The catalyst of the present invention is a ceramic, mixed oxide, nonstoichiometric electrically neutral catalyst containing a rare-earth-type element or mixture thereof, a metal of the first transition series or mixtures thereof, Zirconium, Tin or Thorium or mixtures thereof, oxygen atoms, and optionally an alkaline earth metal or mixture thereof. The transition metal or metals are present as mixed oxides wherein the metal is present in more than one oxidation state. The rare-earth-type element or elements can also be present in more than one oxidation state.

The alkaline earth metals include beryllium, magnesium, calcium, strontium, barium, and radium. In the present invention the preferred alkaline earth elements are magnesium, calcium, strontium, and barium. The rare-earth-type elements are scandium, yttrium and the rare-earth-elements, e.g., lanthanum, cerium, praseodymium, neodymium, promethium, samarium, europium, gadolinium, terbium, dysprosium, holmium, erbium, thulium, ytterbium, and lutetium. In the present invention the preferred rare-earth-type elements have atomic numbers between 20 and 72. The metals of the first transition series include titanium, vanadium, chromium, manganese, iron, cobalt, nickel, copper and zinc. In the present invention the preferred metals of the first transition series include those metals having an atomic number between 21 and 30. At least 0.01% of the transition metal atoms of the oxide catalyst have oxidation states other than +3; i.e., at least 0.01% of the transition metal atoms are present in oxidation states higher or lower than +3. In the preferred embodiment of the present invention, at least 0.1% of the transition metal atoms in a mixture of metal oxides have oxidation states other than +3. Although there is no upper limit to the percentage of metal atoms having oxidation states other than +3, rarely will more than 35% of the transition metal atoms have oxidation states deviating from +3. The rare-earth-type elements may be present in more than one oxidation state, i.e., between and including +2 to +4.

The ceramic, mixed oxide, nonstoichiometric, electrically neutral catalyst of the present invention is a solid crystalline compound at the temperatures at which it is used. Elements represented by W, X, J and Z of formula (I) are present in the catalyst as positively charged ions and the oxygen is present as negatively charged ions. THe chemical bonding between W, X, J, Z and O is most accurately described as being ionic. As a solid chemical compound the catalyst is partially characterized, we believe, by its crystal structure. It differs from the crystal structures of catalysts described as mixtures of oxides such as the hopcalites which are mixtures of metal oxides and not a homogenous mixed oxide compound.

Electrical neutrality in the mixed oxide catalysts of the present invention can be understood in terms of classical theory regarding ionic species and present theories regarding defect chemistry. Electrical neutrality in the present mixed oxide catalyst, in which fractions of the elements represented by Z and J are present as positive ions with charges other than +3, is maintained by a balance of negatively charged and positively charged ionic species and the presence of defects such as positively charged holes, interstitial positive ions, positive ion vacancies, negatively charged electrons and oxygen vacancies. An oxygen vacancy is an empty oxygen lattice site in a crystal structure normally occupied by $O^{-2}$ ions. The defects are particularly important in balancing the X and Z elements having charges other than +3. A fraction of the oxygen vacancy defects may exist as oxygen vacancy defect complexes in which the oxygen vacancy is localized preferentially about a particular positively charged ion. The catalyst exhibits high electrical conductivity at temperatures at which the defects, i.e., holes, vacancies, or electrons are mobile. Ionic conductivity within the catalyst is associated with the mobility of ions such as oxygen ions and is enhanced by the presence of defects such as oxygen vacancies or oxygen vacancy complexes.

It appears that the surprising activity of the present catalyst arises from the nonstoichiometric character of the metal oxide composition contained therein. The present catalyst has a very high electronic conductivity and ionic conductivity. The sum of the electronic conductivity and the ionic conductivity is the electrical conductivity of material and is inversely proportional to the electrical resistance of the material. The present catalyst has an electrical conductivity of about 0.1 ohms$^{-1}$cm.$^{-1}$ to about 1000 ohms $^{-1}$cm.$^{-1}$. The ionic conductivity is a measurement of the ion flow or migration through and over a material. Most materials found in nature have very low ionic conductivities; however, molten salts and salts dissolved in water have very high ionic conductivities. The present catalyst has a high ionic conductivity and will readily permit ions to flow or migrate through and across its surfaces for the distances of 100 angstroms or more. The present ceramic, nonstoichiometric oxidation catalysts also have excellent selective adsorption properties. The present catalysts are relatively good adsorbers of partially oxidized or partially reduced molecular species such as carbon monoxide, sulfur dioxide, the oxides of nitrogen, and hydrogen sulfide, and they are relatively poor adsorbers of fully oxidized or reduced materials, such as carbon dioxide or nitrogen gas. The adsorption qualtities of the present catalyst also appear to arise from its nonstoichiometric nature.

Without intending to limit the invention by the following discussion, it appears that many of the surprising characteristics of the present catalyst can be attributed to its high ionic and electronic conductivity, and selective adsorption characteristics. Under present theory, an effective catalyst must be a good adsorber of reactants and a relatively poor adsorber of the reaction products thereof. If the catalyst is a relatively poor adsorber of reactants, the space velocity of the gas stream containing the reactants and the relative gas pathway length throughout the catalyst are usually adjusted to give the reactants and catalytic surface the optimum contact conditions. The relatively high electronic conductivity of the present catalyst due to either mobile holes or electrons tends to enhance the effective areas of the catalyst by reducing the areas of the space charge regions around adsorbed molecules which tend to become polarized or ionic. Under present theory, it also appears that if the given reaction is a Red-Ox reaction, that is a reaction involving the oxidation of one reactant and the reduction of the other reactant, the site of reduction and the site of oxidation on the catalytic material must be relatively close, such as about 10 A or less, so that electrons and/or molecular ionic species resulting from the partial reduction or oxidation of the reactants can migrate between the two sites to complete the reaction. For example, when the catalyst is to be employed in the oxidation of carbon monoxide with water vapor to form carbon dioxide and hydrogen gas, the carbon monoxide molecule will become attached to an oxidation site and become chemically excited wherein it will readily accept either monoatomic oxygen or ionic oxygen to form carbon dioxide. A water molecule will become attached to a reduction site wherein the water molecule will be split apart to form diatomic hydrogen and monoatomic or ionic oxygen. The former will escape from the catalyst surface while the latter will migrate over the catalytic surface or through the catalyst as oxygen ions to a nearby carbon monoxide oxidation site to combine therewith and form carbon dioxide which will subsequently escape from the surface of the catalyst. If the oxidation and reduction sites are more than 10 A apart, the conventional catalyst generally will not be very effective and will exhibit little catalytic activity. In the present catalyst, the respective reaction site can be separated by distances far exceeding 10 A; for example, the reaction sites can be separated by distances of 100 A or more, because the catalyst has high ionic and electronic conductivity which provides excellent mobility for electrons and atomic and molecular ionic species. Consequently, in the present catalyst electrons or holes can readily flow and migrate from site to site during a given chemical reaction and likewise oxygen ions can migrate and flow from site to site with relative ease.

The present catalysts are prepared by making up an aqueous solution of the corresponding water-soluble salts and the rare-earth-type elements, metals of the first transition series, Zirconium, Tin or Thorium, and alkaline earth metals, if the latter are to be included. Typical water-soluble salts that are employed include the nitrate and halide salts of the rare-earth-type elements, the metals of the first transition series, Zirconium, Tin and Thorium, and the alkaline earth metals. After the aqueous solution is thoroughly mixed, the solution is evaporated at either room temperature or at elevated temperatures to dryness and the resulting residue is calcined for several hours at elevated temperatures, such as temperatures between 600° C. and 1500° C. If the salts lack oxygen atoms, the salt mixture is calcined in the presence of oxygen, i.e., air. The resulting ceramic nonstoichiometric oxidation catalyst is a fine powder which may be sintered to varying degrees. It can be milled, pressed and sintered to any desired shape. Alternatively, the powdered catalyst can be moistened, molded or extruded into a desired shape, and then sintered or fired. Alternatively, the present catalyst can be prepared from the water-insoluble salts, such as the sulfates, carbonates, or oxides of the rare-earth-type elements, the metals of the first transition series, Zirconium, Tin or Thorium, and the alkaline earth metals.

The salts are particulated and thoroughly mixed in their appropriate molar amounts. The resulting mixture of salts is then calcined as described above to prepare the ceramic oxidation catalyst of the present invention. Preferably the calcined material is ground thoroughly and resintered several times to insure a complete solid reaction.

Referring to the above formula (I), the value of $(3\pm m')$ is affected by the oxygen pressure during the calcining step as well as the oxygen fugacity and temperature at which the catalyst is used. If the catalytic starting material is calcined in the absence of oxygen or at low oxygen partial pressures such as 10 mm Hg, the value of the quantity $(3\pm m)$ will be smaller than if the starting catalytic material is calcined at high oxygen pressures such as 700 mm Hg, 3 atmospheres or the like. The value of $m$ describing a specific formulation of a catalyst depends also on the conditions of its catalytic use. For example, if two catalytic processes involve the same temperature but different oxygen fugacities, the value of $m$ will be higher for the process characterized by the higher oxygen fugacity.

The catalyst of formula (I) and the ceramic-mixed oxide catalyst of the following empirical formulas can be employed in several novel oxygenation processes:

$$X_{n'}J_{(1-n)}{}^{Z}O_{(3\pm m)} \quad (II)$$

$$W_{k'}J_{(1-k')}{}^{Z}O_3 \quad (III)$$

wherein W, X, J, Z, O and $m$ are as defined above and $k'$ is a number having a value of between 0 and about 0.05 and $m$ is a number having a value of from 0 to about 0.26. For example, these catalysts can be employed for a preparation of an oxygenated carbon-hydrogen compound selected from the group consisting of organic hydroxyl compounds, organic carbonyl compounds, organic carboxylic acid compounds and organic carboxylic anhydride compounds by reacting a carbon-hydrogen organic compound selected from the group consisting of aromatic organic compounds, organic olefinic compounds, organic acetylenic compounds, organic epoxide compounds, organic hydroxyl compounds, and organic carbonyl compounds with a predetermined amount of an oxygenation agent selected from the group consisting of oxygen and water; and passing the resulting mixture over the catalyst of the above formulas at a predetermined elevated temperature.

Such processes include some of the following illustrated processes:

A. benzene + $O_2$ → phenol + maleic anhydride

B. naphthalene + $O_2$ → phthalic anhydride

C. O-xylene + $O_2$ → phthalic anhydride

D. furan + $O_2$ → maleic anhydride

E. toluene + $O_2$ → benzaldehyde + benzoic acid

F. anthracene + $O_2$ → anthroquinone phenanthrene + $O_2$ → phenanthroquinone

G. alkanes + $O_2$ → 1-alkanals

H. 1-alkanols + $O_2$ → 1-alkanals

I. alkenes + $O_2$ → epoxyalkanes

J. epoxyalkanes + $H_2O$ → alkanediols

K. ethylene + $H_2O$ → 2-ethanol

L. 1-alkynes + $H_2O$ → 2-alkanols

M. acetylene + $H_2O$ → acetone

N. olefins + $O_2$ → fatty acids and/or ketones

O. dialkyl carbinols + $O_2$ → dialkyl ketones

P. propylene + $O_2$ → acrolein

Q. methane + ammonia + $O_2$ → hydrogen cyanide

R. hydrocarbon + NO → $N_2$ + $CO_2$ + $H_2O$

S. CO + $SO_2$ + $H_2O$ → $H_2S$ + $CO_2$

The processes are carried out with an oxygen containing gas, such as air or oxygen gas. The processes are normally carried out in the gaseous state with the reactants and oxygen being passed through a bed of the above catalysts in a carrier gas. However, the processes can be conducted in liquid solids systems employing inert solvents and an oxygen containing gas. Process A is conducted at a temperature between about 300° and about 700° C. The production of maleic hydride is favored when excess oxygen is present, whereas the production of phenol is favored when less than an equal molar amount of oxygen is present.

Process B is normally carried out at a temperature between about 250° and about 600° C., employing naphthalene/air ratios of 1:5 to 1:200. Contact times of between 0.02 and 10 seconds can be used.

Process C is conducted at a temperature between about 300° and about 500° C. employing at least one molar equivalent of oxygen for each mole of orthoxylene; preferably employing 3 or more molar equivalents of oxygen. In this process minor amounts of maleic anhydride are also produced. Contact times of between 0.1 and 5 seconds can be used in Processes C and D.

Process D is conducted at a temperature of about 200° and about 450° C. employing a concentration of around 0.1 to 10 mole-percent furan in an air stream. At least one molar equivalent of oxygen is employed for each mole of furan present.

Process E is conducted at a temperature between about 300° and about 600° C., employing at least 0.25 molar equivalents of oxygen for each mole of toluene; preferably at least 1 mole equivalent of oxygen. Higher processed temperatures and/or molar ratios of oxygen favor the production of benzoic acid over benzaldehyde.

Process F is conducted at temperatures between about 300° and about 700° C., employing an excess of oxygen. The product is anthraquinone when anthracene is the reactant and phenanthraquinone when phenanthrene is the reactant.

Process G is conducted with a molar excess of oxygen at temperatures between about 300° and about 600° C. at elevated pressures of between 1 and 25 atmospheres. The temperature and oxygen concentration are adjusted to maximize the production of the alcohol; however, some of the alcohol is further oxidized to the corresponding aldehyde and/or acid. This process is very valuable for the production of formaldehyde and acetaldehyde or mixed aldehydes from methane, ethane, or natural gas. Alkanes having from 1 to 40 carbon atoms can be employed, though usually the alkanes employed will have 25 or less carbon atoms.

Process H is conducted at a temperature between about 200° and about 400° C., at alkanol concentrations of about 10 mole percent in air. Contact times of between 0.5 and 10 seconds can be used. Some of the alcohol is oxidized to the corresponding carboxylic acid, i.e., alkanoic acid. The alkanol starting material can have 1 or more carbonn atoms, preferably 2 or more carbon atoms.

Process I is conducted at a temperature between about 200° and about 400° C., employing alkene concentrations of 1-10 mole percent of $O_2$ concentrations of 5-80 mole percent in the presence of $N_2$, $CO_2$ or steam. Contact times of between 0.02 and 10 seconds can be used. This process is very valuable for the production of ethylene oxide and propylene oxide from ethylene and propylene.

Process J is conducted at a temperature between about 200° and about 600° C. in the presence of steam. This process can be conducted at atmospheric pressure of one atmosphere or greater. This process provides a convenient method of preparing ethylene glycol and propylene glycol from ethylene oxide and propylene oxide.

Process K is conducted at a temperature between about 200° and about 500° C. in the presence of steam. This process is conducted at elevated pressures up to 300 atmospheres or more employing contact times of between 0.5 and 11 seconds. This process provides a valuable method of producing ethanol from ethylene.

Processes L and M are conducted at a temperature between about 200° and about 600° C. in the presence of steam. This process can also be conducted at elevated pressures up to 300 atmospheres or more.

Process N is conducted at a temperature between about 250° and about 600° C. with at least one molar equivalent of oxygen for each mole of olefin; preferably with a great excess of oxygen. When the carbon atoms of the double bond of the olefin are each substituted with a hydrogen atom, the resulting products are fatty acids. When one or more of the carbon atoms of the double bond are substituted with two alkyl groups, the products are a mixture of the fatty acids and ketones when one carbon atom is substituted with two alkyl groups or a mixture of ketones when both carbon atoms are so substituted.

Process O is conducted at a temperature between about 200° and about 600° C., employing at least 10 mole percent of the dialkyl carbonol (i.e., secondary alcohol) in the oxygen-containing carrier gas. This process is useful for the production of acetone from 2-propanol or methyl amyl ketone (i.e., 2-heptanone) from 2-heptyl alcohol (i.e., 2-heptanol).

Process P is conducted at a temperature between about 200° and about 500° C. at elevated pressures up to 300 atmospheres.

Process Q is conducted at a temperature between about 700° and about 1100° C., employing equal molar amounts of methane and ammonia and three molar equivalents of oxygen to produce hydrogen cyanide and water. This is a very advantageous process for the preparation of hydrogen cyanide from inexpensive, commercially available products.

Process R is conducted at a temperature between about 200° and about 1000° C., employing excess amounts of hydrocarbons. This process offers a convenient way of eliminating the oxides of nitrogen from combustion gas exhausts of automobile engines, other heat engines employing fossil fuels and chemical processes which form nitrogen oxides as an undesired product.

Process S is conducted at a temperature between about 200° and about 800° C. in the presence of steam. This process provides an advantageous method of eliminating sulfur dioxide and carbon monoxide from the exhaust gases of engines employing fossil fuels containing sulfur or sulfur-bearing compounds. The combustion of the engine is controlled so that equal amounts of CO and $SO_2$ are produced.

As with any catalytic gas phase process, contact time between the reactant and the catalyst can be varied over a wide range such as between about 0.01 to about 10 seconds, to maximize production to the desired product and minimize side product production. The optimum contact time for a process, employing a particular catalyst, reactants, and reaction temperature, can be determined by conventional methods and experiments.

For purposes of this invention, "organic hydroxyl compounds" are organic compounds containing the HO-group, such as phenol, primary alcohols (i.e., 1-alkanols) and secondary alcohols (i.e., 2-alkanols and dialkyl carbonols). For purposes of this invention, "organic carbonyl compounds" include ketones (i.e., alkanones), quinones and aldehydes (i.e., alkanols). For purposes of this invention "organic carboxylic acid compounds" include the fatty acids (i.e., alkanoic acids), such as acetic acid, propanoic acid, caprylic acid, decanoic acid and the like. For purposes of this invention, "organic carboxylic anhydride compounds" include maleic anhydride, phthalic anhydride and the like. For purposes of this invention "aromatic organic compounds" include benzene, naphthalene, xylene, toluene, anthracene, phenthrene, and derivatives thereof. For purposes of the present invention "organic olefinic compounds" include alkenes, such as ethylene, propylene and the higher alkenes. For purposes of the present invention "organic acetylenic compounds" (i.e., alkynes) include acetylene, and mono-and di-alkyl substituted acetylene derivatives. Organic epoxide compounds (i.e., epoxy alkanes) include ethylene oxide, propylene oxide and the like.

The catalysts of the following empirical formula:

$$W_k X_{n'} J_{(1-k-n)} Z_O^{ZO(3\pm m)} \qquad (IV)$$

wherein W, X, J, Z, O, k, m and n are as defined above and can be employed in the oxidation of a wide variety of molecular species. For example, the above catalysts can be utilized in the following oxidation reactions:

U. $2CO + O_2$  $2CO_2$

V. $2H_2 + O_2$  $2H_2O$

—continued

W. Hydrocarbons and Oxygenated Hydrocarbons such as Aldehydes, Ketones, Ethers, Alcohols, and Carboxylic acids $+ \frac{1}{2} nO_2 \longrightarrow {}_mCO_2 + pH_2O$ wherein n, m and p are integers having a value of 1 or more.

X. $2SO_2 + O_2 \longrightarrow 2SO_3$

Y. $2H_2S + 3O_2 \longrightarrow 2SO_2 + 2H_2O$

Z. $4NH_3 + 4O_2 \longrightarrow 2N_2O + 6H_2O$

AA. $4NH_3 + 5O_2 \longrightarrow 4NO + 6H_2O$

BB. $2NO + O_2 \longrightarrow 2NO_2$

CC. $2CO + 2NO \longrightarrow 2CO_2 + N_2$

DD. $CO + H_2O \longrightarrow CO_2 + H_2$

EE. $4CO + 2SO_2 \longrightarrow 4CO_2 + S_2$

FF. $4H_2S + 2SO_2 \longrightarrow 3S_2 + 4H_2O$

GG. Hydrocarbons + CO + $CO_2$ + $H_2O$ + $N_2$ + $O_2$
(slight excess) $\longrightarrow CO_2 + H_2O + N_2 + O_2$ (residual)

Reaction U-BB and GG normally will be carried out with atmospheric oxygen, i.e., with air. In such cases, in each of these oxidation reactions there will be little concomitant oxidation of the atmospheric nitrogen to the nitrogen oxides such as a nitric oxide. However, reactions U-BB and GG can be carried out with any oxygen containing gas. Reaction U can be conducted with only a trace of carbon monoxide and requires only a slight excess of the stoichiometric amount of oxygen needed for the complete combustion oxidation of the carbon monoxide to carbon dioxide. The reactants, i.e, the carbon monoxide and oxygen, are passed through a bed of the catalyst at a temperature between about 100° C. and about 1000° C. Reaction V can be conducted with only a trace amount of hydrogen and requires only a slight excess of a stoichiometric amount of oxygen needed for the oxidation of the hydrogen. In this reaction the reactants are passed through a bed of the catalyst at a temperature between about 100° C. and about 500° C. Reaction W can be practiced with hydrocarbons, such as methane, butane, benzene, or the like, aldehydes such as acetaldehyde or hexanol, ketones, such as acetone or diacetone alcohol, alcohols, such as methyl alcohol, propyl alcohol, or the like, carboxylic acids, such as acetic acid, decanoic acid, or mixtures of the above. This reaction requires an excess of the stoichiometric amount of the oxygen needed for the complete combustion of the above-described reactants. The reactants and oxygen are passed over the catalyst at temperatures between about 100° C. and about 1000° C. At higher temperatures the reaction rate is appreciably increased and permits very high space velocities. Reaction X can be conducted with trace amounts of sulfur dioxide and requires an excess of the stoichiometric amount of oxygen needed for the oxidation of the sulfur dioxide. The reaction is conducted through a bed of the catalyst at a temperature between about 120° C. and about 800° C. Reaction Y can be conducted with a trace amount of hydrogen sulfide and requires an excess of the stoichiometric amount of oxygen needed for the oxidation of the hydrogen sulfide. The reaction is conducted by bringing the reactants in contact with the catalyst at a temperature between about 100° C. and about 700° C. Reaction Z can also be conducted with trace amounts of ammonia and requires an excess of the stoichiometric amount of oxygen needed for the oxidation of the ammonia. The reaction is carried out by bringing the reactants in contact with the catalyst of the present invention at a temperature between about 100° C. and about 400° C., preferably between about 250° C. and about 400° C. Reaction AA is a very useful reaction and provides a method of making nitric oxide, the first stage in the manufacture of nitric acid. The reaction requires only a slight excess of the stoichiometric amount of oxygen needed to oxidize the ammonia to nitric oxide. The reaction is conducted at temperatures between about 100° C. and about 1000° C., preferably at a temperature of about 400° C. or higher. Reaction BB represents the second stage in the manufacture of nitric acid from ammonia. The reaction is conducted at temperatures between about 100° C. and about 400° C. Reaction CC is also a very useful reaction and it provides a route for the elimination of both carbon monoxide and nitric oxide from the exhaust gas of industrial plants and motorized vehicles utilizing fossil fuels. Both reactants can be present in trace amounts and can be present in equal stoichiometric amounts. The reaction is carried out in the presence of the catalyst at a temperature between about 200° C. and about 1000° C. When the reaction is conducted in the presence of oxygen or atmospheric oxygen, reactions U and BB are favored and the principal by-products will be carbon dioxide and nitrogen dioxide. Reaction DD is also a useful reaction and provides an alternative route for the elimination of carbon monoxide in exhaust gases produced by the combustion of fossil fuels. Both reactants can be present in trace amounts and either can be in excess. This reaction is also useful for commercial production of hydrogen. The reaction is conducted in contact with the catalyst at a temperature between about 150° C. and about 500° C. If this reaction is conducted in the presence of atmospheric oxygen, reaction U is favored and the principal reactants are carbon dioxide and water from the combustion of hydrogen and atmospheric oxygen. Reactions X and Y provide a means of inexpensively producing sulfur trioxide for sulfuric acid production from sulfur dioxide and/or hydrogen sulfide. The reactions can be conducted with pure oxygen or with oxygen enriched air. Reaction Z provides a means of inexpensively producing nitrous oxide. This reaction can be conducted with pure oxygen or with oxygen enriched air. Reaction GG is a reaction between atmospheric oxygen and an exhaust gas from industrial plants or motor vehicles burning fossil fuels with an oxygen deficiency. The exhaust gas will contain hydrocarbons and/or aldehydes, ketones, alcohols, carboxylic acids, and the like, carbon monoxide, carbon dioxide, water vapor, and atmospheric nitrogen. The reaction is conducted with a slight excess of atmospheric oxygen, that is a slight excess of the stoichiometric amount of oxygen needed for completely combusting the hydrocarbons or other like organic species and carbon monoxide to $CO_2$ and $H_2O$. The effluent gas will contain carbon dioxide, water vapor, atmospheric nitrogen and residual oxygen and will be substantially free of hydrocarbons, carbon monoxide, and oxides of nitrogen, particularly nitric oxide. The exhaust gases are put in contact with the catalyst of the present invention at a temperature between about 200° C. and about 700° 1 C., preferably about 400° C.

Reactions EE and FF represent useful reactions for recovering $SO_2$ as elemental sulfur by catalytic oxidation of CO and $H_2S$ in the absence of oxygen. Reaction temperature is normally between 100° C. and 800° C. The lower reaction temperatures are preferred if the sulfur is subsequently separated from the catalyst by vaporization or dissolution.

As described above, the above catalysts of formulas I and III are very effective oxidation catalysts for the harmful gaseous pollutants found in the exhaust gases of industrial plants and motorized vehicles utilizing fossil fuels. Accordingly, the catalyst can be used to provide methods of eliminating these pollutants from exhaust gases. For example, one method of eliminating or substantially reducing the nitric oxide, carbon monoxide, and hydrocarbon pollutants from the exhaust gases generated by the combustion of fossil fuels, such as natural gas, gasoline, oil stock and/or coal will comprise the following steps: burning the fossil fuel in an oxygen deficiency environment at a temperature between about 1800° C. and about 850° C. to produce an exhaust gas containing carbon dioxide, carbon monoxide, water vapor, unburned or partially burned fossil fuel and atmopheric nitrogen with the carbon dioxide and carbon monoxide being present in the ratio of about 100 to between about 1 and about 11. The combustion of the fossil fuel produces usable heat energy which in turn is employed to produce steam for steam turbines or expand the gases in a reciprocal engine or gas turbine. After the combustion gas has performed its energy function, its temperature will have dropped to between 300° C. and 700° C. The resulting cooled combustion gas will then be combined with a slight excess of atmospheric oxygen, i.e, at least a 1% excess of the stoichiometric amount of atmospheric oxygen needed to fully oxidize the remaining uncombusted or partially combusted fossil fuel and carbon monoxide in the combustion gas. The resulting air combustion gas mixture will then be passed through a bed of the catalyst at a temperature between about 300° C. and about 700° C. to fully oxidize the carbon monoxide and fossil fuel. The effluent gas will contain carbon dioxide, water vapor, atmospheric and residual oxygen. The effluent gas will be substantially free of all fossil fuels or remnants thereof, carbon monoxide and nitric oxide. When the first combustion step is conducted at 1200° C. and the subsequent catalytic treatment is conducted at 600° C. the resulting effluent gas will contain less than 10ppm of fossil fuels or remnants thereof, less than 50 ppm of carbon monoxide and less than 60 ppm of nitric oxide.

In sharp contrast the present industrial plants, such as steam-generating plants which burn fossil fuel and use a single-step combustion process employing excess oxygen, produce an exhaust gas containing 500 ppm of fossilized fuel or remnants thereof, more than 250 ppm of carbon monoxide and more than 340 ppm of nitric oxide. These pollutants, as described above, are a major contributor to photochemical smog.

The situation is motorized vehicles is even worse. Less than 10% of the motorized vehicles are properly adjusted and have their smog emission devices working at optimum conditions. The remainder of the vehicles are not properly tuned, have inoperative or poorly operating smog emission devices and/or faulty mufflers. The motorized vehicles emit vast quantities of unburned or partially combusted gasoline, massive amounts of nitric oxygen and appreciable amounts of carbon monoxide.

The present invention contemplates a method utilizing the above catalysts for operating a motorized vehicle which will emit an exhaust gas which is substantially free of fossil fuels or remnants thereof, carbon monoxide and nitric oxide. Preferably the gasoline employed in the motorized vehicle would be lead free. However gasolines containing less than 1 gram of lead per gallon could be utilized in the method described herein since the catalysts are relatively insensitive to lead contamination.

The reciprocal engine will be adjusted to run on a rich mixture, that is, the engine will be run with an overall deficiency of oxygen. The engine can be adjusted so that it runs on an oxygen deficiency of between 10% and 0.1% so as to limit the formation of nitric oxide. The exhaust gases from the combustion chambers of the engine are vented or piped into a catalytic muffler containing the ceramic, mixed oxide catalyst of the present invention. The exhaust gases would contain unburned fuel or partially burned fuel, carbon dioxide, carbon monoxide, water vapor, and atmospheric nitrogen. Just before entering the catalytic muffler, the combustion gases could be combined with at least 1% of excess of atmospheric oxygen, that is, at least 1% in excess of the stoichiometric amount of oxygen needed for the complete combustion of the carbonaceous material in the combustion gas. The resulting mixture would then be passed through the catalytic muffler at a temperature between about 100° C. and about 700° C. The resulting effluent gas would contain carbon dioxide, water vapor, atmospheric nitrogen, and residual oxygen. The effluent gas would be substantially free of all fuel and remnants thereof, carbon monoxide, and nitric oxide.

The above catalysts are ideally suited to the above-described method for two reasons: (1) the catalysts are relatively unaffected by metallic substances, such as lead, and (2) the present catalysts will selectively oxidize carbonaceous material, such as carbon monoxide and hydrocarbons, in preference to atmospheric nitrogen over a broad range of temperatures.

The present catalyst can also be used to produce a two-step catalytic process for removing gaseous pollutants from fossil fuel exhausts, that is, the exhaust gases produced by the combustion of fossil fuels. In this method, the fossil fuel can be burned with a stoichiometric amount of atmospheric oxygen or a slight deficiency. The fossil fuel can be burned at a temperature of 1000° C. or higher. The fossil fuel is burned with a deficiency of oxygen in order that at least as much carbon monoxide, on a molar basis, is produced as nitric oxide, preferably at least twice as much carbon monoxide is produced; nitric oxide production is disproportionately increased at high combustion temperatures. The combustion gases will contain fossil fuel, partially combusted fossil fuel, carbon dioxide, carbon monoxide, water vapor, nitric oxide and atmospheric nitrogen. If fossil fuel contains sulfur or sulfur containing compounds, sulfur and hydrogen sulfide will also be found in the combustion gases. After the combustion gases have fulfilled their energy function, they will have cooled to about 700° C. or less. The cooled combustion gases are passed through a bed of the catalyst wherein the carbon monoxide is oxidized by nitric oxide and water to carbon dioxide. If the fuel contains sulfur containing compounds, the resulting effluent gas may be cooled to recover the sulfur. The resulting effluent gas is then mixed with a slight excess of atmospheric oxygen and passed through a second bed of catalyst of the present invention wherein the fossil fuel, partially combusted fossil fuel, remaining carbon monoxide, remaining nitric oxide, hydrogen sulfide, and sulfur are fully oxidized yielding an exhaust gas consisting essentially of carbon dioxide, water vapor, sulfur trioxide, atmospheric nitrogen, nitrogen dioxide and residual atmospheric oxygen. The exhaust gases will be essentially free of the gaseous pollutants, i.e., oxides of nitrogen and sulfur. This method is particularly applicable for use on motorized vehicles and high temperature industrial plants wherein a large quantity of nitric oxide is produced during the combustion step.

The catalysts of formulas (III) and (IV), wherein $m$ has a value other than 0, are prepared in the same manner as the catalyst of formula (I). The catalysts of formulas (I) and (IV), wherein $m$ has a value of 0, can be prepared by conventional methods, such as the method disclosed by G. H. Zonker, Phillips Research Reports, 24, 1-14 (1969). The maximum value of $k$ and $k''$ in the catalysts of formulas (I), (IV) and (V), infra, is reduced when $n$ and $n'$ in the formulas have values of 0 because the solubility of Zirconium, Tin and Thorium in the catalyst composition is reduced in the absence of alkaline earth metals in the catalyst composition. The above catalysts can be formed and utilized in various states and shapes, such as powdered form, pellets, flakes, and the like. The catalyst can be sintered to varying degrees. For the industrial plant use or catalytic muffler use, the catalyst can be used as a powder, as pressed sintered pellets, macaroni-shaped tubes, flat or curved flakes, honeycombed plates, and the like. The catalyst also can be used on a support such as a ceramic refractory, glass or high-melting metal support substance. As metioned above, the powdered catalyst can be pressed into shape and fired or sintered to fix the shape. Alternatively, the powder material can be made plastic by mixing with water or with an organic binder and extruded into any desired shape and sintered or fired into that shape. In another alternative method, the catalyst can be made into a liquid paint or ink which can be used to coat a support or walls, such as muffler walls, and the like. After the coating is complete, the catalytic paint or ink can be dried and fired to fix the coating to the underlying support or wall. If an extremely thin layer, such as $10^3$ A, of the catalyst on a particular support is required, the catalyst can be coated on the support by ionic sputtering.

The operating temperature ranges cited are particularly wide for the catalyst. This results from the low, high and overlapping temperatures over which specific examples of the catalyst of the present invention are characterized by high electronic and ionic conductivities which contribute to the electrical conductivity. This desired feature permits optimization with regard to chemical and thermal stability for a specific application.

The following examples are included to further illustrate the present invention and are not intended as limitations thereof.

EXAMPLE 1

An aqueous mixture of 49.5 moles of a lanthanum nitrate ($La(NO_3)_3$), 50.0 moles of cobalt nitrate ($Co(NO_3)_2$) and 0.5 mole of $Th(NO_3)_4$ is prepared from the corresponding lanthanum, cobalt and thorium nitrate salts. The solution is boiled and evaporated to dryness; the resulting residue is calcined in air for 7 hours at 1200° C. to produce a fine powder having the following empirical formula:

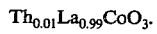

$Th_{0.01}La_{0.99}CoO_3$.

A substantially identical catalyst is prepared by employing the corresponding chloride salts in place of the nitrate salts in the above procedure.

The above powdered catalyst is moistened with distilled water and glycerine to prepare a thick paste which is extruded into a macroni-shaped tubes. The tubes are air-dried for 48 hours and then fired at 1300° C. for 3 hours.

EXAMPLE 2

An aqueous solution containing 1 mole of tin chloride, 1 mole of barium chloride, 8 moles of yttrium chloride and 10 moles of titanium chloride was prepared by dissolving the corresponding chloride salts in 100 liters of water. The resulting aqueous solution was evaporated to dryness under a vacuum. The resulting residue was calcined for 10 hours at 1200° C. under an atmosphere of air to produce a fine powder having the following empirical formula:

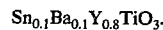

$Sn_{0.1}Ba_{0.1}Y_{0.8}TiO_3$.

The resulting powder was pressed into cylindrical pellets measuring 5 millimeters by 2.5 centimeters in a hydraulic press at 10,000 psi and sintered at 1100° C.

EXAMPLE 3

A catalyst is made by the procedure of Example 1 by calcining under an inert argon gas atmosphere to produce a fine ceramic powder having the following empirical formula:

$Th_{0.01}La_{0.99}CoO_{(3-m)}$.

wherein $m$ has a value between 0 and 0.26.

EXAMPLE 4

A catalyst is made by the procedure of Example 1 employing 6 moles of chromium nitrate in place of cobalt nitrate and calcining under a 100% oxygen gas atmosphere to produce a ceramic powder having the following empirical formula:

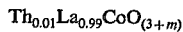

$Th_{0.01}La_{0.99}CoO_{(3+m)}$ wherein $m$ has a value between 0 and 0.26.

EXAMPLE 5

An aqueous solution containing 1.0 mole of Zirconium chloride, 3 moles of calcium bromide, 6.5 moles of a mixture of cerium nitrate, neodymium nitrate, and lanthanum nitrate, and 10 moles of nickel chloride are prepared by heating 75 liters of distilled water to boiling and adding the above corresponding salts of zirconium, calcium, cerium, neodymium, lanthanum and nickel. The solution is boiled to dryness and the residue is calcined under a nitrogen gas atmosphere for 5 hours at 1150° C. to produce a crusty residue of the empirical formula:

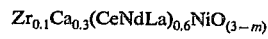

$Zr_{0.1}Ca_{0.3}(CeNdLa)_{0.6}NiO_{(3-m)}$ wherein $m$ is a value between 0 and 0.26, which powdered on scraping. The resulting powder is moistened with water and starch to produce a thin paste. Neutral alumina pellets are rolled through the paste to coat the catalyst thereon. The coated pellets are air-dried and fired at 1250° C. for 18 hours to bond the catalyst coating to the pellets.

EXAMPLE 6

A 100 liter aqueous solution containing 0.001 moles of thorium chloride, 0.1 mole of calcium chloride, 9.889 moles of a mixture of rare earth nitrates wherein the rare earth elements have atomic numbers from 57 to 71, and 10 moles of a 50:50 mixture of chromium and manganese nitrate. The resulting aqueous solution is boiled to dryness at 1 mm. of Hg vacuum and the resulting residue is calcined for 8 hours at 800° C. under an atmosphere of air at 2 atmospheres pressure. The resulting catalyst powder is pressed into spherical shapes measuring 5 millimeters in diameter and sintered at 1100° C.

EXAMPLE 7

To 1000 liters of water, there are added 1 mole of zirconium nitrate, 28 moles of strontium chloride, 70 moles of ytterbium chloride, 1 mole of lutetium chloride, and 100 moles of vanadium chloride. The resulting mixture is heated and stirred to form a solution which is filtered and evaporated to dryness at room temperature under vacuum to form a dry residue. The residue is calcined to 1050° C. for 8 hours under an atmosphere of air to produce a ceramic powder.

The powder is moistened and pressed into flat sheets 2.5 millimeters thick; the pressed sheets are dried and fired at 1200° C. for 9 hours to form ceramic sheets which are thereafter broken into 1 centimeter flakes.

The other catalysts disclosed herein [the catalyst of formulas (I), (II) and (III)] can be prepared by the processes of the above examples by employing the appropriate molar amounts of transition metal and rare-earth salts and optionally salts of the alkaline earth metals or Zirconium, Thorium or Tin.

EXAMPLE 8

A mixture of 0.2 g. of stannic oxide, 4.3 g. of magnesium acetate, 28.8 g. of barium carbonate, 69.0 g. of lanthanum carbonate, 57.4 g. of erbium oxide, and 59.7 g. of ferric oxide is milled into a fine powder. The resulting powder is pressed into rods 0.1 cm. in diameter and fired at 1200° C. under an atmosphere of nitrogen for 15 hours to produce catalytic ceramic rods.

The rods are broken up to form pellets measuring about 1 cm. in length.

EXAMPLE 9

A mixture of 25.4 g. of thorium sulfate ($Th(SO_4)_2$), 266 g. of lanthanum sulfate ($La_2(SO_4)_3$), 50 g. of chromic anhydride, and 77.5 g. of cobalt sulfate ($CoSO_4$) is milled to a fine powder. The powder is moistened with a 70:3:30 mixture of water, glycerine and gum arabic to form a paint. The catalytic paint is coated on fired alumina plates and allowed to air-dry. The coated plates are then fired in air at 1100° C. for 36 hours to produce a ceramic catalytic plate.

EXAMPLE 10

An air stream containing 10 ppm carbon monoxide was heated to 200° C. and passed through a bed of a ceramic, mixed oxide nonstoichiometric, electrically neutral catalyst having the following empirical formula:

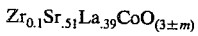

$$Zr_{0.1}Sr_{.51}La_{.39}CoO_{(3\pm m)}$$

wherein $m$ has a value of from 0 to about 0.26. The catalyst bed measured 1 centimeter in diameter and 10 centimeters in length and the velocity of the gas was 10 centimeters per second. The effluent gas was cooled to room temperature and analyzed with gas liquid chromatography using a thermal conductivity detection cell and a 30 foot column containing molecular sieve which showed that the resulting air stream has less than 5 parts ppm. of carbon monoxide and no nitric oxide. Substantially similar results will be obtained by employing the other catalysts described above in the temperature ranges wherein they are characterized by having significant electrical conductivities.

Substantially the same results are obtained by employing a ceramic, mixed oxide, nonstoichiometric, electrically neutral catalyst of the following formula:

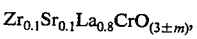

$$Zr_{0.1}Sr_{0.1}La_{0.8}CrO_{(3\pm m)},$$

wherein $m$ has a value of from 0 to about 0.26 and heating the air stream to 400° C.

EXAMPLE 11

An air stream containing 5% carbon monoxide and 10% water is passed through a bed of sintered pellets of a ceramic catalyst of the present invention having the following empirical formula:

$$Th_{0.00002}Ca_{0.1}La_{0.9}NiO_{(3\pm m)},$$

wherein $m$ has a value of from 0 to about 0.26. The catalyst bed measures 1 centimeter by 15 centimeters and is heated to about 350° C. The velocity for the gas stream is 12 centimeters per second. The effluent gas contains less than 10 parts per million (ppm) carbon monoxide and virtually no nitric oxide.

EXAMPLE 12

An air stream containing 15% sulfur dioxide is passed through a bed of ceramic flakes of a ceramic non-stoichiometric catalyst having the following empirical formula:

$$Sn_{0.05}Y_{0.95}FeO_{(3\pm m)},$$

wherein $m$ has a value of from 0 to about 0.26. The catalyst is prepared according to the procedure of Example 7. The catalytic bed measures 1 centimeter in diameter and 12 centimeters in length and is heated to 250° C. The effluent gas contains sulfur trioxide and is substantially free of sulfur dioxide, and nitric oxide.

Substantially identical results are obtained when the catalyst is maintained at a temperature between 300° C. and 450° C.

EXAMPLE 13

An air stream containing 4% hydrogen sulfide is passed through a bed of a powdered ceramic nonstoichiometric catalyst of the following empirical formula:

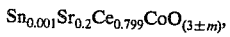

$$Sn_{0.001}Sr_{0.2}Ce_{0.799}CoO_{(3\pm m)},$$

wherein $m$ has a value of from 0 to about 0.26. The catalyst can be prepared according to the procedure of Examples 1, 3, or 4. The gas stream is heated to 400° C. and the velocity of 20 centimeters per second is maintained through the catalytic chamber which measures .8 centimeters in diameter by 12.5 centimeters in length. The effluent gas contains sulfur trioxide, some sulfur dioxide, and water and is substantially free of hydrogen disulfide and nitric oxide.

EXAMPLE 14

An air stream containing 5% ammonia is heated to 900° C. and passed through a bed of a powdered, ceramic, nonstoichiometric catalyst of the following empirical formula:

$$Zr_{0.00001}(YLaCeNdSm)NiO_{(3\pm m)}$$

wherein $m$ has a value between 0 and 0.26. The catalyst chamber measures 10 centimeters in diameter by 1 meter and the velocity of the gas stream is maintained at 7.5 liters per second. The effluent gas stream is essentially free of ammonia and contains nitric oxide (as nitric oxide and nitrogen dioxide) and water as the major by-products. When this process is conducted at a temperature around 275° C., the major by-products are nitrous oxide and water.

An air stream containing 10% nitric oxide and heated to 225° C. was utilized in place of the air stream containing ammonia in the above method to yield an effluent gas stream containing less than 0.2% nitric oxide; the major product is nitrogen dioxide and its dimer.

EXAMPLE 15

A gas stream containing equal portions of carbon monoxide and nitric oxide is passed through a catalytic chamber containing a bed of sintered ceramic nonstoichiometric catalytic pellets of the following empirical formula:

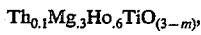

$$Th_{0.1}Mg_{.3}Ho_{.6}TiO_{(3-m)},$$

wherein $m$ has a value of from 0 to about 0.26. The gas stream is maintained at 650° C. and passed through the catalytic chamber at a sufficient space velocity to insure that the reactants are in the catalytic chamber for approximately 1/10 of one second. The effluent gas is substantially free of carbon monoxide and nitric oxide and consists essentially of carbon dioxide and nitrogen gas.

The above carbon monoxide-nitric oxide gas stream is replaced with an air stream containing 1% carbon monoxide, 500 ppm nitric oxide, and 2% water. The effluent gas stream is substantially free of carbon monoxide, contains less than 30 parts per million nitric oxide and consists essentially of atmospheric gases and carbon dioxide.

EXAMPLE 16

The burners of a steam turbine generating plant boiler are operated with natural gas fuel so that the maximum flame temperature is 1500° C. The natural gas is burned in an oxygen deficiency to yield a combustion gas containing carbon monoxide, atmospheric nitrogen, water vapor, and carbon dioxide. The combustion gas also contains some nitric oxide and hydrocarbons. The ratio of $CO_2$ to CO in the gas is adjusted to a ratio of 95:5 by controlling the air supply. The combustion gas, after being employed in producing high-pressure steam, is combined with a 1% excess of atmospheric oxygen at a temperature of about 600° C. and passed through a catalytic chamber containing the catalyst of Example 4 at a space velocity sufficient to insure that the combustion gas is in contact with the catalyst for about 0.10 second to yield a stack gas which is substantially free of nitric oxide and carbon monoxide and contains principally carbon dioxide, water and atmospheric nitrogen. When the fuel is burned with a greater oxygen deficiency to yield a $CO_2$ to CO ratio of 90 to 10, an even cleaner stack gas with respect to nitric oxide is obtained.

With increasing temperatures for the initial combustion stage, increasing portions of nitric oxide will be emitted in the combustion gases. The following table shows the parts per million of nitric oxide present in the combustion gas at various combustion temperatures for the first stage of combustion.

TABLE

| Combustion Temperature | Parts per million of nitric oxide in combustion gas |
|---|---|
| 1500° C. | 150 ppm |
| 1400° C. | 32 ppm |
| 1300° C. | 0.9 ppm |
| 1200° C. | 0.09 ppm |

The above method provides a method for public utilities to produce power with fossil fuels and yet emit a stack gas containing a minimal amount of nitric oxide, carbon monoxide, and unburned fuel. At present, most public utility plants producing energy from fossil fuel emit an exhaust gas containing from about 200 to about 1500 ppm of nitric oxide. In many areas of the country, such as Los Angeles, public utilities are a major contributor, up to 10%, of the nitric oxide in the air.

The above method can be employed utilizing natural gas, oil fuel, or coal with substantially the same results.

EXAMPLE 17

A carburetor and the timing of a reciprocal engine, which burns a gasoline containing 0.5 gm of lead/gallon, is adjusted so that the engine, when operating in its normal operating temperature, burns a slightly rich fuel-air mixture having about a 1% oxygen deficiency. The exhaust or combustion gas from the cylinders of the reciprocal engine are vented through manifolds and exhaust pipes into a mixing chamber wherein the combustion gases are mixed with a slight excess of atmospheric oxygen, that is a 1% excess of the stoichiometric amount of oxygen needed to fully burn the carbonaceous material, i.e., unburned and partially burned gasoline and carbon monoxide, present in the combustion gases. The resulting mixture is then vented into a catalytic muffler containing an alumina honeycomb matrix coated with a catalyst having the following empirical formula:

$$Zr_{0.1}Sr_{.1}La_{.8}CoO_{(3\pm m)}$$

wherein $m$ has a value of from 0 to about 0.26. The catalytic chamber is designed such that the exhaust gas will travel through the muffler in about 0.1 second when the engine is working at its maximum revolution rate. The combustion gas has a temperature of above 300° C. when it comes in contact with the catalyst. The resulting effluent gas will contain less than 500 parts per million of carbon monoxide, and will be substantially free of gasoline or partially burned gasoline.

EXAMPLE 18

The combustion gases from a steam turbine generating plant burning fossil fuels in a 2.1% oxygen deficiency contains carbon dioxide, carbon monoxide, sulfur, hydrogen sulfide, nitric oxide, atmospheric nitrogen, water vapor, and unburned or partially burned fossil fuel. The combustion gas, which is heated to about 700° C., is passed through a catalytic chamber containing the catalyst of Example 6 at such a rate such that the catalyst and all the combustion gas come into contact. The gaseous pollutants in the resulting effluent gas are substantially reduced. In particular, the amount of carbon monoxide and nitric oxide contained therein are substantially reduced because the nitric oxide and water vapor have oxidized the carbon monoxide to carbon dioxide. The resulting effluent gas which has now cooled down to about 100° C. and the sulfur are collected by electrostatic precipitation. The resulting gas is heated to aproximately 250° C. and combined with a 0.7% excess of the stoichiometric amount of oxygen needed to fully oxidize the unburned fuel, partially burned fuel, the sulfur-containing compounds and the remaining carbon monoxide. The resulting air and effluent gas mixture is passed through a second catalytic chamber containing the catalyst of Example 17. The second catalytic chamber is designed such that the gaseous mixture and the catalysts are in contact for approximately 0.1 to 0.5 seconds. The resulting effluent gas consists essentially of carbon dioxide, water vapor, atmospheric nitrogen and residual oxygen. The effluent gas contains less than 80 parts per million of nitric oxide, less than 50 parts per million of carbon monoxide, and is substantially free of nitrogen dioxide and unburned or partially burned fuel.

EXAMPLE 19

A gas stream containing nitric oxides and hydrocarbons is passed through a catalytic chamber containing a bed of the catalyst of the formula described in Example 20. The gas stream is maintained at a temperature around 700° C. and passed through the catalytic chamber at a sufficient space velocity to insure that the reactants are in contact with the catalyst for at least 0.1 second. The exhaust gas from the catalyst bed contains nitrogen gas and the unreacted hydrocarbons.

EXAMPLE 20

A carrier gas containing between 50% and 0.5% benzene is passed through a bed of a catalyst of the following formula (V) at a temperature between about 325° and 500° C. at a sufficient velocity to insure the contact time between the catalyst and the carrier gas is about 0.1 seconds:

$$W_{k'}X_nJ_{(1-k'-n')}ZO_{(3\pm m)} \quad (V)$$

wherein W, X, J, Z, O and $m$ are as defined above, and $k''$ is a number having a value of from 0 to about 0.1; and $n'$ is a number having a value of from 0 to about 0.51, provided when $n'$ has a value of O, $k''$ has a value of from 0 to about 0.05. The off-gas from the catalyst bed is cooled to about 0° C. and passed through a mist eliminator to condense the material in the carrier gas for collection. The collected material contains principally maleic anhydride together with lesser amounts of phenol and benzene. The compounds are separated from each other by conventional techniques.

EXAMPLE 21

An air stream containing about 50% benzene vapor is passed through a bed of a catalyst of the formula of Example 20 at a temperature between about 275° and 700° C., at a sufficient space velocity to insure that the air stream and the catalyst have a contact time of about 0.1 second. The off stream from the catalyst bed contains phenol and lesser amounts of benzene and maleic anhydride which are separated by conventional techniques. The ratio of phenol to benzene and maleic anhydride is increased with increasing reaction temperatures.

EXAMPLE 22

An air stream containing between about 20% to about 0.5% naphthalene is passed through a bed of catalyst of the formula in Example 20, at a temperature of between about 270° and 600° C. at a sufficient space velocity to insure that the air stream in the catalyst has a contact time of between about 0.02 and 10 seconds. The off-gas from the catalyst bed contains phthalic anhydride and unreacted naphthalene; the two compounds are separated by conventional separation techniques.

EXAMPLE 23

An air stream containing about 5% ortho-xylene is passed through a bed of catalysts of the formula shown in Example 20, at a temperature of between about 320° and 500° C. at a sufficient space velocity to insure a contact time between about 0.1 and 5 seconds between the ortho-xylene and the catalyst. The off-gas contains primarily phthalic anhydride and minor amounts of maleic anhydride and unreacted ortho-xylene which are separated by conventional techniques.

EXAMPLE 24

An air stream containing about 1% furan is passed through a bed of catalyst having the formula described in Example 20, at a temperature of between about 250° and about 400° C., at a space velocity sufficient to insure contact time between the air stream and the catalyst of between about 0.1 and 5 seconds. The off-gas from the catalyst bed contains primarily maleic anhydride and smaller amounts of furan, the two compounds are separated by conventional techniques.

EXAMPLE 25

An air stream containing about 10% toluene is passed through a bed of catalyst of the formula described in Example 20, at a temperature of about 500° C. at a space velocity sufficient to insure that toluene and the catalyst have a contact time of at least 0.15 seconds. The off-gas from the bed of catalyst contains unreacted toluene, benzaldehyde and benzoic acid. The production of benzoic acid can be favored by increasing the process temperature and/or increasing the contact time between the catalyst and the toluene and/or increasing the $O_2$/toluene ratio. The formation of benzaldehyde can be favored by lowering the process temperature and/or decreasing the contact time between the toluene and the catalyst and/or decreasing the $O_2$/toluene ratio.

EXAMPLE 26

An air stream containing about 1% anthracene is passed through the catalyst having the formula described in Example 20, at a temperature of about 500° C. and at a space velocity sufficient to insure that the contact time between the air stream and the catalyst is at least about 1 second. The off-gas from the catalyst bed contains anthraquinone and unreacted anthracene which are separated by conventional techniques. By employing phenanthrene in the above process, the off-gas will contain phenanthraquinone.

EXAMPLE 27

An air stream containing about 10-mol % methanol is passed through a bed of catalyst having the formula described in Example 20, at a temperature of between about 250° and 500° C., at a space velocity sufficient to insure contact time between the air stream and the catalyst of between about 0.5 and 10 seconds. The off-gas contains primarily formaldehyde and a small amount of unreacted methanol which are separated by conventional techniques. By employing the higher alkanols, such as ethanol or decanol, the corresponding higher alkanals, such as acetaldehyde and decanal, are produced.

EXAMPLE 28

An air stream containing about 5% natural gas consisting essentially of methane, ethane, propane, butane, small amounts of pentane is passed through a bed of the catalyst of the formula described in Example 20, at a temperature of between about 350° and 500° C. at a space velocity sufficient to insure a contact time of at least 1 second between the gas stream and the catalyst. The gas stream is pressurized between about 1 and 25 atmospheres. The off-gas from the catalyst bed contains the corresponding aldehydes or alkanals of the hydrocarbons. For example, methanal is produced from methane and ethanol is produced from ethane.

EXAMPLE 29

A carrier gas containing between about 1 and 10 mol % of ethylene and between about 5 and 80 mol % oxygen is passed through a bed of a catalyst of the formula described in Example 20, at a temperature of between about 200° and 350° C., at a sufficient space velocity to insure a contact time between the catalyst and the carrier gas of between 0.02 and 1 second. The off-gas from the catalyst bed contains ethylene oxide and lesser amounts of ethylene which are separated by conventional techniques.

EXAMPLE 30

A carrier gas containing about 1% propylene oxide and 10% steam is passed through a bed of a catalyst of the formula described in Example 20, at a temperature of between about 150° and 250° C., at a sufficient space velocity to insure contact time between the catalyst and the carrier gas is at least one second. The off-gas of the catalyst bed contains propylene glycol (1,2-propanediol) and propylene oxide which are separated by conventional methods. By employing ethylene oxide in this process, ethylene glycol is obtained.

EXAMPLE 31

A carrier gas under a pressure up to about 300 atmospheres and containing about 10% propylene and about 10% steam is passed through a bed of a catalyst of the formula described in Example 20, at a temperature of between about 250° and 450° C., at a sufficient space velocity to insure the contact time between the catalyst and the carrier gas is between about 1 and 10 seconds. The off-gas from the catalyst bed contains isopropyl alcohol and propylene which are separated by conventional techniques. By employing ethylene in this process, ethanol is obtained.

EXAMPLE 32

A carrier gas containing about 10% methyl acetylene and 10% steam is passed through a bed of a catalyst of the formula described in Example 20, at a temperature of about 400° C., at a sufficient space velocity to insure that the contact time between the catalyst and the carrier gases is at least about 5 seconds. The off-gas from the catalyst bed contains isopropyl alcohol and methyl acetylene which are separated by conventional techniques.

EXAMPLE 33

A carrier gas containing about 1% acetylene and about 10% steam is passed through a bed of a catalyst of the formula described in Example 20, at a temperature of between about 250° and 450° C., under an elevated pressure of between about 1 and 300 atmospheres. The off-gas from the catalyst bed contains acetylene and acetone which are separated by conventional techniques.

EXAMPLE 34

A carrier gas containing about 1% oleic acid is passed through a bed of a catalyst of the formula described in Example 20, at a temperature of about 500° C., at a sufficient space velocity to insure the contact time between a catalyst and a carrier gas is about 1 second. The off-gas contains pelargonic, azelaic and oleic acids which are separated by conventional techniques.

EXAMPLE 35

A carrier gas containing about 5% methyl propyl carbinol is passed through a bed of a catalyst of the formula described in Example 20, at a temperature of about 500° C., at a sufficient space velocity to insure the contact time between the catalyst and the carrier stream is about one second. The off-gas contains methyl propyl ketone and methyl propyl carbinol which are separated by conventional techniques.

EXAMPLE 36

An air stream, pressurized between about 1 and 200 atmospheres, containing about 3% propylene, is passed through a catalyst of the formula described in Example 20, at a temperature between about 250° and 500° C., and at a sufficient space velocity to insure the contact time between the catalyst and the carrier gas is between about 1 and 10 seconds. The off-gas from the catalyst bed contains acrolein and propylene which are separated by conventional techniques.

EXAMPLE 37

An inert carrier stream containing equal molar amounts of methane and ammonia, and about 3 molar equivalents of oxygen, is passed through a bed of a catalyst of the formula described in Example 20, at a temperature of about 1000° C. The off-gas from the catalyst bed contains unreacted methane ammonia and oxygen together with hydrogen cyanide, carbon monoxide, carbon dioxide and water which are separated by conventional techniques.

EXAMPLE 38

An exhaust gas from the combustion of fossil fuel containing carbon monoxide and sulfur dioxide in water together with other constituents, such as carbon dioxide, is passed through a catalyst of the formula described in Example 20, at a temperature between about 200° and about 800° C., at a sufficient space velocity to insure the contact time between the catalyst and the carrier gas of about one second. The off-gas from the catalyst bed contains hydrogen sulfide and carbon dioxide together with unreacted carbon monoxide or sulfur dioxide, depending on whether carbon monoxide or sulfur dioxide, respectively, is in molar excess in the combustion gas.

EXAMPLE 39

The exhaust gases from a fossil fuel heat engine containing carbon monoxide and sulfur dioxide are passed through a catalytic chamber containing a catalyst of the following formula at a temperature of about 400° C.:

$$Zr_{.05}Be_{.05}Tb_{.85}Tm_{.05}MnO_{(3-m)}$$

wherein $m$ has a value of from 0 to about 0.26. The gases are passed through the catalyst at a sufficient space velocity to insure that the available carbon monoxide reacts with the available sulfur dioxide to yield carbon dioxide, sulfur and the unreacted reactant, if any.

By employing a gas stream containing hydrogen sulfide and sulfur dioxide in the above process, sulfur, water and the unreacted reactant, if any, are obtained.

EXAMPLE 40

The life supporting oxygen containing atmosphere of an enclosed system, as for example in a submarine or space vehicle, is passed through a catalytic chamber containing the catalyst of the following formula heated to a temperature of about 200° C.:

$$Sn_{.05}Gd_{.95}VO_{(3+m)}$$

wherein $m$ has a value of from 0 to about 0.26. Hydrogen present in the atmosphere is oxidized to water to reduce the hydrogen concentration in the atmosphere to 10 ppm. or less.

I claim:

1. A process for the oxidation of carbon monoxide to carbon dioxide with an inorganic oxidizing agent selected from the group consisting of water, nitric oxide and sulfur dioxide, which comprises:
   combining the carbon monoxide with a predetermined amount of said oxidizing agent to give at least a stoichiometric amount of the oxidizing agent for the oxidation of the carbon monoxide to carbon dioxide; and
   passing the mixture over a ceramic catalyst of the following empirical formula at an elevated temperature:

$$W_kX_mJ_{(1-k-n)}ZO_{(3\pm m)},$$

wherein:
   W is Zirconium, Tin or Thorium or mixture thereof;
   X is an alkaline earth metal or mixture thereof;
   J is Scandium, Yttrium, a rare-earth element or mixture thereof;
   Z is a metal of the first transition series or a mixture thereof, at least 0.01% of said metal having an oxidation state other than +3;
   $k$ is a number having a value of between 0 and about 0.1;
   $m$ is a number having a value of from 0 to about 0.26; and
   $n$ is a number having a value from 0 to about 0.51, provided when $n$ has a value of 0, $k$ has a value between 0 and about 0.05.

2. The process according to claim 1 wherein the carbon monoxide is oxidized by combining it with a predetermined amount of water vapor to give at least a stoichiometric amount of water for the oxidation of carbon monoxide to carbon dioxide; and passing the resulting mixture over said ceramic catalyst at a temperature between about 150° C. and about 500° C. to obtain carbon dioxide and hydrogen.

3. The process according to claim 1 wherein the carbon monoxide is oxidized by combining it with a predetermined amount of nitric oxide to give at least a stoichiometric amount of nitric oxide for the oxidation of carbon monoxide to carbon dioxide; and passing the resulting mixture over said ceramic catalyst at a temperature between about 700° C. and about 1000° C. to obtain carbon dioxide and nitrogen.

4. The process according to claim 1 wherein the carbon monoxide is oxidized by combining it with a predetermined amount of sulfur dioxide to give at least a stoichiometric amount of sulfur dioxide for the oxidation of carbon monoxide to carbon dioxide; and passing the resulting mixture over said ceramic catalyst at a temperature between about 100° C. and about 800° C. to obtain carbon dioxide and sulfur.

* * * * *